US008298563B2

(12) United States Patent
Reneker et al.

(10) Patent No.: US 8,298,563 B2
(45) Date of Patent: Oct. 30, 2012

(54) POLYMER NO DONOR PREDRUG NANOFIBER COATING FOR MEDICAL DEVICES AND THERAPY

(75) Inventors: Darrell Reneker, Akron, OH (US); Daniel J. Smith, Stow, OH (US)

(73) Assignee: The University of Akron, Akron, OH (US)

( * ) Notice: Subject to any disclaimer, the term of this patent is extended or adjusted under 35 U.S.C. 154(b) by 1088 days.

(21) Appl. No.: 10/597,272

(22) PCT Filed: Jan. 24, 2005

(86) PCT No.: PCT/US2005/002266
§ 371 (c)(1),
(2), (4) Date: Jul. 11, 2008

(87) PCT Pub. No.: WO2005/070008
PCT Pub. Date: Aug. 4, 2005

(65) Prior Publication Data
US 2008/0286321 A1   Nov. 20, 2008

Related U.S. Application Data

(60) Provisional application No. 60/538,333, filed on Jan. 22, 2004.

(51) Int. Cl.
*A61F 2/02* (2006.01)
(52) U.S. Cl. .................................................. 424/423
(58) Field of Classification Search .................... None
See application file for complete search history.

(56) References Cited

U.S. PATENT DOCUMENTS

| 4,043,331 A | 8/1977 | Martin et al. |
| 4,878,908 A | 11/1989 | Martin et al. |
| 5,519,020 A | 5/1996 | Smith et al. |
| 5,770,645 A | 6/1998 | Stamler et al. |
| 5,814,656 A | 9/1998 | Saavedra et al. |
| 6,429,012 B1 | 8/2002 | Kraus et al. |
| 6,685,956 B2 | 2/2004 | Chu et al. |
| 6,737,447 B1 * | 5/2004 | Smith et al. ............ 523/105 |

FOREIGN PATENT DOCUMENTS

| EP | 1300424 A1 | 4/2003 |
| WO | WO/96/32136 | 10/1996 |
| WO | WO/98/03267 | 1/1998 |
| WO | 0127365 A1 | 4/2001 |
| WO | WO/01/26702 | 4/2001 |

OTHER PUBLICATIONS

Reynolds, M.M., et al., "Nitric Oxide-Releasing Hydrophobic Polymers: Preparation, Characterization, and Potential biomedical Applications", Free Radical Biology and Medicine, Elsevier Science, 2004-06-019, vol. 37, No. 7.
Pulfer, Sharon, Incorporation of Nitric Oxide-Releasing Crosslinked Polyethyleneimine, John Wiley & Sons, Inc. (1997).
Doshi, Jayesh, Electrospinning Process and Applications of Electrospun Fibers, Journal of Electrostatics 35 (1995) 151-160.
Smith, Daniel, Nitric Oxide-Releasing Polymers Containing the [N(O)NO] Group, J. Med. Chem (1996), 1148-1156.

* cited by examiner

*Primary Examiner* — Carlos Azpuru
(74) *Attorney, Agent, or Firm* — Renner Kenner Greive Bobak Taylor & Weber

(57) ABSTRACT

The present invention relates to nanofibers that produce therapeutic amounts of nitric oxide after a delay period, which allows time to install or implant the device into a patient. The nitric oxide release is thus localized to the area of the organism where NO dosing is indicated. The delay time is achieved by cospinning the NO-producing fiber with a fiber that tends to sequester the former's NO-producing functional groups. Fibers of the present invention may be incorporated into medical devices such as stents or other implantable medical devices to prevent the formation of adhesions or scarring in the area of the implant.

19 Claims, No Drawings

POLYMER NO DONOR PREDRUG NANOFIBER COATING FOR MEDICAL DEVICES AND THERAPY

BACKGROUND OF THE INVENTION

The present invention relates to coatings and medical devices that deliver therapeutic amounts of nitric oxide (NO) to areas where NO dosing is indicated. More particularly, the present invention relates to fibrous materials that evolve nitric oxide after a delayed activation. The nanofibers of the present invention function to both carry and sequester reagents, which can react to release NO gas, when water, blood or other fluids known as activators are brought into contact with the nanofiber. The sequestration action slows the diffusion of activators to an NO precursor and thus delays the precursor's conversion to NO.

NO is known to inhibit the aggregation of platelets and to reduce smooth muscle proliferation, which is known to reduce restenosis. When delivered directly to a particular site, it has been shown to prevent or reduce inflammation at the site where medical personnel have introduced foreign objects or devices into the patient, such as stents or other implantable devices.

Researchers have sought various ways to deliver NO to damaged tissue and to tissues and organs at risk of injury. NO can be delivered systemically, but such delivery can bring undesired side effects with it U.S. Pat. No. 5,814,656. Ideally, NO should be delivered in a controlled manner specifically to those tissues and organs that have been injured or are at risk of injury. The present invention fills this need by providing a coatings and medical devices that release NO after a delay, which gives the physician time to implant the device. Thus, for the most part only tissues requiring NO treatment receive doses of NO.

Insoluble polymeric NONOates have also been generally described in Smith et al. U.S. Pat. No. 5,519,020 to topically deliver NO to specific tissues. However, this patent does not discuss impeding activation such that there is substantially a delay between the time the device is first applied and the time when NO production becomes significant. The use of polymeric NONOates as coatings on implantable medical devices is also disclosed in Stamler et al. U.S. Pat. No. 5,770,645. This patent is similarly deficient in that it too fails to discuss any mode of delaying nitric oxide production. The device of '645 is essentially active from the moment it is first implanted because it lacks an activator-impeding element. In contrast, the present invention incorporates just such an element, which is specifically directed to slowing or delaying the activation of the nitric oxide predrug.

Probably, the most closely related art is the inventors' own U.S. Pat. No. 6,737,447, which discloses a polymeric coating for medical devices that releases nitric oxide in a controlled manner. However, the distinction between this and the present invention is that '447's mode of controlled release is its use of bisepoxide to crosslink the coating thus constricting that material's porosity thus slowing the diffusion of activators into and nitric oxide out of the coating. In contrast the present invention utilizes a second fiber having either a more hydrophobic character, or a buffering effect to impede, slow or delay the activation of the nitric oxide precursor.

SUMMARY OF THE INVENTION

The present invention relates to coatings and medical devices that deliver therapeutic amounts of nitric oxide (NO) to areas where NO dosing is indicated. More particularly, the present invention relates to fibrous materials that evolve nitric oxide after a delayed activation. The nanofibers of the present invention function to both carry, and sequester and/or buffer the environment surrounding NO precursor (hereinafter referred to as a predrug) reagents, which release NO when water, blood or other fluids known as activators are brought into contact with the precursor. The sequestration action slows the diffusion of activators to an NO precursor and thus delays the precursor's conversion to NO, and it results from the hydrophobic character of the second fiber. Additionally, the buffering action creates a more basic environment immediately surrounding the NO precursor, which results in a slower conversion rate to nitric oxide. In any given embodiment either the sequestration or the buffering effect, or both may be used to impede NO production. In any case both the sequestration and buffering effects arise from the incorporation of a fiber hereinafter referred to as a "second fiber".

The present invention uses a smaller amount of NO predrug than prior innovations to produce an effective amount of NO because it is spatially constrained to the locus where NO dosing is indicated, whereas some prior innovations have allowed NO to circulate in the blood stream. Thus, in relatively small quantities the present invention could evolve therapeutic amounts of NO and may be useful as a stent coating, a balloon used to open the stent, catheters, in products such as wound dressings for the treatment of fungal or parasitic infections, or for treatment of poorly healing wounds.

The central concept of the present invention could be applied in other areas, namely CO or peroxide production, sterilization, and chemical therapies. Particularly, using a second fiber to sequester a precursor compound thus impeding an activator's access thereto and thus delaying the release of a product compound could be applied in other areas, namely CO or peroxide production, sterilization, and chemical therapies.

The present invention relates to a medical device comprising a polymeric carrier fiber component, a nitric oxide predrug component, and a second fiber functioning to sequester the predrug from activating species. The present invention further relates to a medical device, wherein the medical device is selected from the group consisting of a vascular graft, a stent, a catheter, a wound dressing, and a surgical thread. The present invention further relates to a medical device, wherein the polymeric carrier fiber component comprises at least one secondary amine moiety. The present invention further relates to a medical device, wherein the polymeric carrier fiber component is selected from the group consisting of a polyethyleneimine, a polyethyleneimine grafted to a polysaccharide backbone, and a poly(ethyleneimine) salt. The present invention further relates to a medical device, wherein the polymeric carrier fiber component comprises a poly(ethyleneimine) fiber. The present invention further relates to a medical device, wherein the polymeric carrier fiber component comprises an electrospun nanofiber. The present invention further relates to a medical device, wherein the nitric oxide predrug component is selected from the group consisting of a diazeniumdiolate, an O-alkylated diazeniumdiolate, and an O-derivatized diazeniumdiolate. The present invention further relates to a medical device, wherein the nitric oxide predrug component comprises a diazeniumdiolate. The present invention further relates to a medical device further comprising an activator. The present invention further relates to a medical device, wherein the activator is a proton donor. The present invention further relates to a medical device, wherein the activator is a buffer selected from the group consisting of phosphates, succinates, carbonates, acetates, formates, propionates, butyrates, fatty acids, and amino acids. The present invention further relates to a medical device, wherein the activator is water. The present invention further relates to a medical device further comprising a mobile phase. The present invention further relates to a medical device, wherein the mobile phase is capable of transporting an activator such that it contacts the nitric oxide predrug component. The present invention further relates to a medical device, wherein the mobile phase is selected from the group consisting of water, methanol, ethanol, propanols, butanols, pentanols, hexanols, phenols, naphthols, polyols, acetic acid, N,N-dimethylformamide, dimethyl sulfoxide, dimethylacetamide, and tetrahydrofuran, hexanethylphosphoramide. The present invention further relates to a medical device further comprising a substantially hydrophobic second fiber. The present invention further relates to a medical device, wherein the second fiber is selected from the group consisting of polyurethane, polyamide, polyethylene, polypropylene, polyesters, saturated polyesters, polyethylene terephthalate, polytetrafluoroethylene, perfluoroethylene, polystyrene, polyvinyl chloride, and polyvinyl pyrolidone.

The following terms are specially defined. Predrug, as used herein, means any compound that will be modified to form a drug species, wherein the modification may take place either inside or outside of the body, and either before or after the predrug reaches the area of the body where administration of the drug is indicated. Polymeric carrier fiber component comprises at least one of any fiber capable of reversibly reacting with nitric oxide to form functional groups, located on the fiber, that amount to nitric oxide predrug components. Second fiber component, as used herein, refers to one or more fibers that sequester the predrug from activating agents such as blood or lymph while the device is being inserted or implanted into, or otherwise applied to the patient. The term activator comprises any compound that stimulates the nitric oxide predrug component to produce nitric oxide.

DETAILED DESCRIPTION OF ILLUSTRATIVE EMBODIMENTS

The present invention is directed to a coating and device that produces a therapeutic amount of nitric oxide and delivers it to areas of an organism where NO dosing is indicated. In general, the present invention takes the form of a mixture of fibers. Some of the fibers of the mixture are derivatized so that they will evolve NO when stimulated to do so. Importantly, other "second" fibers are not derivatized, rather their purpose is to provide structure to the mixture of fibers and/or to sequester the NO yielding portions of the derivatized fibers from species that tend to stimulate NO evolution. Alternatively, their function is to buffer the environment of the NO predrug so as to slow its conversion to NO. In doing so the second fiber tends to regulate the rate at which NO evolves from the invention, and impedes activation of the device's constituent NO-yielding moieties.

An illustrative embodiment of the present invention comprises a coating on a metal stent for opening a blood vessel. Such a device must be implanted in a patient by feeding it through a blood vessel beginning from a point some distance away from the area where the stent will ultimately reside. Therefore the tissues at the point of insertion are at some distance from the site where nitric oxide dosing is indicated. Thus tissues at the insertion point, as well as all points between insertion and the locus where the stent is ultimately implanted, are preferably not exposed to NO. The present invention accomplishes this through the foregoing built-in NO production delay.

In general, the present invention comprises three elements: (1) a polymeric carrier fiber component, (2) a nitric oxide predrug, and (3) a second fiber component. The polymeric carrier fiber component comprises any fiber or fiber having sites capable of reversibly reacting with nitric oxide to form functional groups, located on the fiber, that amount to nitric oxide predrug components. Acceptable fibers tend to contain secondary amine moieties inasmuch as secondary amines are known to react with nitric oxide to form diazeniumdiolates, which undergo a first order reaction evolving nitric oxide. In order to stimulate the NO evolving reaction the nitric oxide predrug component, i.e. the diazeniumdiolate for example, must chemically contact and interact with a source of protons hereinafter referred to as an activator. It is expected that many classes of compounds can be activators inasmuch as only very minimal Bronsted acidity is necessary to stimulate the decomposition reaction. Thus water, alcohols, polyols and the like are all acidic enough to act as activators. Other activator species include body fluids, especially blood, lymph, bile and the like. In order to substantially restrict NO exposure to those areas where NO dosing is indicated activation is impeded to allow for the time required to implant or insert the device into the patient. Such impedance is achieved through the action of the second fiber, which either sequesters the predrug from species that tend to stimulate the predrug-to-drug reaction, or buffers the environment around the predrug so as to slow the rate of its conversion to drug form. Preferably, the three elements of the present invention can comprise a single fiber in that the fiber functions as a carrier, includes the predrug, and has a "second" fiber component that provides structure and/or sequesters the predrug. But the elements can be provided as two or three separate components.

Polymeric Carrier Fiber Components

The polymeric carrier fiber component comprises any fiber capable of reversibly reacting with nitric oxide to form functional groups, located on the fiber, that amount to nitric oxide predrug components. Acceptable fibers tend to contain secondary amine moieties inasmuch as secondary amines are known to react with nitric oxide to form diazeniumdiolates, which undergo a first order reaction evolving nitric oxide (I-II). Acceptable carrier fiber components comprise polymers including but not limited to polyetyleneimine, polypropyleneimines, polybutyleneimines, polyurethanes, and polyamides. Further acceptable carrier fiber components include any of the foregoing polymers grafted to an inert backbone, e.g. polyethyleneimine grafted to a an otherwise relatively inert backbone such as a polysaccharide backbone, especially a cellulosic backbone. Still further acceptable carrier fiber components include any fiberizable material comprising secondary amine moieties.

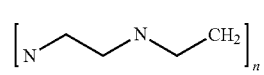

Polyethyleneimine

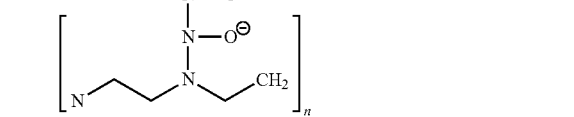

NO Derivatized Polethyleneimine

A preferred material for forming a carrier fiber component in accordance with the present invention is high density linear polyethyleneimine (I-II) having a weight average molecular weight of greater than about 200,000. Linear PEI is soluble in common solvents like water and ethanol. PEI fibers may be formed by electrospinning processes known in the art. It will also be appreciated by those skilled in the art that PEI fibers may be formed in accordance with the present invention by methods other than electrospinning. Any method of forming organic polymers into fibers known in the art may be used. For instance, extrusion methods such as wet spinning, dry spinning, melt spinning, and gel spinning are all acceptable methods of forming fibers in accord with the present invention. Generally, finer denier fibers yield fiber mats having greater surface area and thus more nitric oxide predrug moieties, which generally results in better performance. Accordingly, electrospinning is the preferred method of manufacturing PEI fibers.

In general the present invention may take the form of a nonwoven fiber mat wherein polymeric carrier fibers and second fibers are cospun so that they are more or less randomly distributed. The present invention may also take the form of a layered nonwoven fiber mat, wherein the carrier fiber is spun onto a substrate and then substantially covered and sequestered by spinning a second fiber. In either case the nonwoven fiber mat may take the form of a coating on a medical device such as a stent.

Nitric Oxide Predrug Components

In the most general terms, the nitric oxide predrug component of the present invention comprises any chemical entity that yields nitric oxide when stimulated to do so by an activator of the present invention. It is appreciated in the art that these predrug components may take several forms including but not limited to diazeniumdiolates (sometimes referred to as NONOates). It is further appreciated in the art that these predrug components may take the form of O-alkylated diazeniumdiolate, or any O-derivatized diazeniumdiolate where the O-derivative may be converted back to the diazeniumdiolates. Such O-derivatized NONOates are generally more stable than salts. Particularly, the energy of activation of the decomposition reaction is generally substantially higher than that of the non-O-derivatized form. Thus, the derivative tends to either not evolve NO in the absence of an enzymatic activator, or to extend the half-life of the NONOate significantly. The non-O-derivatized diazeniumdiolate functional group, i.e. the salt, is a preferred nitric oxide predrug component of the present invention, and is known to decompose by a first order mechanism in the presence of a proton source, i.e. activators.

Reacting PEI with NO ordinarily results in the formation of diazeniumdiolates, which causes the PEI to lose its solubility in ethanol, and in some cases become insoluble in water. When the NO modified PEI polymers are exposed to water they begin to decompose in predictable ways resulting in the release of NO. A typical NO release profile from a PEI fiber mat is generally short, one to two days being a representative time.

Activators

Generally, activators comprise any compound that stimulates the nitric oxide predrug component to produce nitric oxide. Where diazeniumdiolate is the predrug, acceptable activators comprise proton sources, i.e. Bronsted acids. Representative activators consistent with the present invention include without limitation: water, body fluids such as blood, lymph, bile and the like; and methanol, ethanol, propanols, butanols, pentanols, hexanols, phenols, naphthols, polyols, and the like. Further activators within the scope of the present invention comprise common aqueous acidic buffers including without limitation phosphates, succinates, carbonates, acetates, formates, propionates, butyrates, fatty acids, and amino acids, and the like. Preferred activators include without limitation: water, body fluids such as blood or lymph, alcohols, and common aqueous acidic buffer solutions.

Mobile Phases

It will be appreciated by those skilled in the art that the nitric oxide predrug component and the activator may be spatially separated in a manner that requires a mobile fluid to carry the activator to the predrug and thus stimulate the reaction. Hereinafter such fluids are referred to as mobile phases. In many cases the activator is itself a fluid under ordinary operating conditions so an additional carrier fluid is not necessary. In such cases the mobile phase may be omitted. Acceptable mobile phases include any fluid that is capable of transporting an activator to a predrug component in a manner that places the activator in physicochemical contact with the predrug so that the nitric oxide yielding reaction is enabled.

Mobile phases are a component of the present invention, which are only required when the activator is unable to reach the nitric oxide predrug component without assistance. In general, the mobile phase carries the activator to the nitric oxide predrug so that the two make physicochemical contact resulting in the evolution of nitric oxide. Thus it follows that mobile phases do not principally participate in the decomposition in the manner of a catalyst or reagent, rater they are principally activator delivery vehicles. However, the fact that a compound is capable of stimulating the predrug's NO evolution does not prevent it from being classified as a mobile phase as well. For example, water is acidic enough to cause a NONOate to evolve NO, but it may also dissolve and carry an activator such as phosphate to the NONOate predrug thus acting as a delivery vehicle for phosphate. Accordingly, water may be doubly classified as both an activator and a mobile phase.

Acceptable mobile phases comprise fluids, preferably liquids, capable of carrying activators to the predrug component. More particularly, mobile phases within the purview of the present invention are liquids capable of dissolving activators. Still more particularly, where diazeniumdiolates are the predrug component, the mobile phase is preferably a more or less polar liquid, especially polar solvents such as water, methanol, ethanol, propanols, butanols, pentanols, hexanols, phenols, naphthols, polyols, acetic acid, N,N-dimethylformamide, dimethyl sulfoxide, dimethylacetamide, and tetrahydrofuran, hexamethylphosphoramide, and the like.

Second Fibers

The function of second fibers is to sequester the predrug from activating agents, buffer the area surrounding the NO predrug, or both thus slowing the predrug's conversion to drug form. Accordingly, second fibers may have substantial hydrophobic character. In this way they amount to a physical barrier that the activator must cross in order to react with the predrug and release NO. Alternatively, the second fiber may have basic functional groups that render the environment surrounding the NO predrug more basic thereby slowing its conversion to drug form. Thus, NO production is substantially limited to the area of the patient where NO dosing is indicated.

Second fibers are also in part used to dilute the NO-releasing fibers, i.e. the polymeric carrier fiber component. Often the output of the NO-releasing fibers is too rapid to create a coating or device comprising them alone. Rather, it would often make sense to embed or cospin the NO-producing fibers into a matrix of fibers made from another polymer, i.e. the second fibers. Appropriate materials for second fibers depends upon the application, but in general they are chosen based upon their capacity to sequester the predrug from activators as well as mechanical durability, and biodegradability properties.

Additionally, second fibers may be structural fibers in the sense that they may add strength to the materials allowing it to be formed into various objects such as a free-standing patch, tube or the like.

Polymers from which second fibers may be made include without limitation polyurethane, polyamide, polyethylene, polypropylene, polyesters, saturated polyesters, polyethylene terephthalate, polytetrafluoroethylene, perfluoroethylene, polystyrene, polyvinyl chloride, and polyvinyl pyrolidone. Preferably the second fiber is substantially hydrophobic.

Consider a stent coating as an illustration of the function of second fibers. A stent coated only with NO modified PEI fibers would have a rapid NO output. Therefore the coating would substantially expose tissues to NO that are not at risk of injury and for which NO dosing is not indicated. In contrast, if a polyurethane such as TECOPHILIC is electrospun with the PEI to form a stent coating, the PEI's NONOate functional groups do not contact the patient's blood immediately because it takes time for the aqueous body fluids to penetrate the polyurethane doped coating.[1]

[1] TECOPHILIC is a trademark of Noveon IP Holdings Corp denoting thermoplastic polyurethane compounds for use in the manufacture of hydrophilic plastic articles In a preferred embodiment polyethyleneimine nanofibers are electrospun onto a medical device or device component along with polyurethane second fibers. The nanofibers are then exposed to NO gas such that at least a portion of the PEI's secondary amine moieties react with NO to form diazeniumdiolate functional groups. In another preferred embodiment the PEI is exposed to NO prior to electrospinning, thus the electrospun PEI fiber already contains diazeniumdiolate functional groups. In either case the PEI's NONOate functional groups are sequestered by the polyurethane nanofiber and thus shielded from moisture and other activators until the device is implanted. NO gas evolves upon exposure to biological fluids such as blood, lymph, or sweat; or upon exposure to other activators such as physiological buffers, alcohols, or polyols.

In another embodiment any of the foregoing fibers may be spun onto any medical device including but not limited to stents, angioplasty balloons, catheters, and the like. The fibers may also be spun into nonwoven fiber mats as in, for example, transdermal patches, bandages and the like. In still another embodiment the nitric oxide-yielding entity may be sequestered within the polymeric carrier fiber as in the manner of a precipitate. In still another embodiment fiber denier is controlled so as to regulate the output of NO. For instance smaller diameter fibers may contain more nitric acid predrug component thus smaller diameter fibers tend to have a higher NO output. In still another embodiment the second fibers comprise biodegradable or bioabsorbable materials so that a device or portion thereof made with such second fibers tends to be consumed by the subject organism's own body. In still another embodiment the present invention takes the form of a vascular graft. Another embodiment of the present invention takes the form of a catheter. Still another embodiment of the present invention is a wound dressing as in the manner of a bandage.

In order to demonstrate the practice of the present invention, the following example is provided. The embodiments should not, however, be viewed as limiting the scope of the invention. The claims will serve to define the invention.

The synthesis of linear polyethylenimine (L-PEI) was performed in a 2 L three-necked round-bottomed flask with a drain stopcock in the bottom; it was equipped with a thermometer well, reflux condenser, addition funnel, stirrer, and heating mantle. With rapid stirring of 300 ml deionized water, the Poly (2-ethyl-2-ozaxoline) or polyethyloxazoline 500,000 MW (49.6 g, 0.5 mol base) was slowly added, and the mixture was stirred at room temperature for several hours until the polymer had dissolved. To the stirred solution was slowly added 75 g (0.75 mol) sulfuric acid; the mixture was then stirred under 100° C. reflux. After 18 h, the agitation was increased and 200 ml additional deionized water was added. A distilling head was placed on the flask and about 250 ml of the distillate (water and propionic acid) was removed.

At reflux, 250 ml of 50% of sodium hydroxide was added with stirring over 15 min. A viscous yellow (light cream color) polymer phase stuck to the stirrer shaft, and 200 ml deionized water was added. The caustic layer was drained off, and the polymer mass was stirred with 500 ml deionized water. The polymer was dissolved by stirring at 85°-100° C. with 500 ml deionized water. The solution was poured into a beaker and the polymer was crystallized upon cooling. An additional 250 ml deionized water was added; the white gelatinous mass was stirred vigorously, and the polymer was collected by suction filtration.

The polymer was redissolved in 1.3 L of deionized water at 90° C. and again allowed to crystallize, at which point it was filtered. This process of recrystallization and filtration was performed three times. The polymer was first air-dried then oven dried at 40-60° C. and at 25 mm Hg for 5 days to give a yield of 97%. The resulting semi-transparent solid was stored in an amber container kept in a dissecator. The polymer was characterized using NMR, which established that the polymer is linear polyethylenimine.

The resulted semi-transparent solid was poured into a flask to be dissolved in a hot (55-60° C.) chloroform/methanol solution (90%:10% ratio). Once the polymer is completely dissolved, the solution was then transferred into another flask with an excess of ethyl ether to precipitate the polymer. As soon as the polymer solution is in contact with the ether, a white fine precipitate starts to show up. The ether is decanted and the particles are dried under nitrogen. The bigger pieces of LPEI are scratched off the wall, mixed with dry ice (or liquid nitrogen), smashed in a mortar, and then transferred to a flask in order to dry it under a stream of nitrogen. The product is passed through a 20 mesh sieve and then stored in an amber container kept in a dissecator.

The NO modified compound was prepared by putting L-PEI as a particle, with acetonitrile in a high pressure glass bottle (ACE Glass) with a magnetic stir bar. The stirred mixture was purged with argon gas, depressurized, and then connected to a NO gas tank. The mixture was then brought to 80 psi of NO and left to react for 13 days under continuous stirring. After this time the NO gas was released, and the mixture was purged and flushed with argon. The product was isolated by the removal of solvent using a roto evaporator and washed with ethyl ether three times. The resultant particles where analyzed using a Sievers 280i NO Analyzer.

LPEINO particles (0.05 g) were suspended into a 20% (w/w) solution of Tecoflex polymer in ethanol and THF (80:20). The polymer solutions (LPEINO particles/Tecoflex polymer) were spun from a conical metal reservoir, which was suspended with copper wire that was connected to the power supply, and the targeted plate was covered with aluminum foil; to facilitate the removal of the fiber. The diameter of the metal cone used to spun the nanofiber was 1.5 mm, the gap distance was 33 cm, and a voltage of 30 kV at room temperature. Same procedure was used to make the fiber with Tecophilic polymer. Each of these released NO over time when subjected to activators.

Various modifications and alterations that do not depart from the scope and spirit of this invention will become apparent to those skilled in the art. This invention is not to be duly limited to the illustrative embodiments set forth herein.

What is claimed is:

1. A medical device comprising: a polymeric carrier fiber, wherein the carrier fiber is capable of reversibly reacting with nitric oxide; a nitric oxide predrug; and a second fiber, wherein said second fiber functions to sequester said predrug from reactive species.

2. The medical device of claim 1, wherein the medical device is selected from the group consisting of a vascular graft, a stent, a catheter, and a wound dressing.

3. The medical device of claim 1, wherein the polymeric carrier fiber comprises at least one secondary amine moiety.

4. The medical device of claim 3, wherein the polymeric carrier fiber is selected from the group consisting of a polyethyleneimine, a polyethyleneimine grafted to a polysaccharide backbone, and a polyethyleneimine salt.

5. The medical device of claim 3, wherein the polymeric carrier fiber comprises a polyethyleneimine fiber.

6. The device of claim 3, wherein the polymeric carrier fiber comprises an electrospun nanofiber.

7. The device of claim 1, further comprising an activator.

8. The device of claim 1 further comprising a mobile phase.

9. The device of claim 8, wherein the mobile phase is capable of transporting an activator such that it contacts the nitric oxide predrug component.

10. The device of claim 9, wherein the mobile phase is selected from the group consisting of water, methanol, ethanol, propanols, butanols, pentanols, hexanols, phenols, naphthols, polyols, acetic acid, N,N-dimethylformamide, dimethyl sulfoxide, dimethylacetamide, and tetrahydrofuran, hexamethylphosphoramide.

11. The device of claim 1, wherein said second fiber is substantially hydrophobic.

12. The device of claim 1, wherein the second fiber is selected from the group consisting of polyurethane, polyamide, polyethylene, polypropylene, polyesters, saturated polyesters, polyethylene terephthalate, polytetrafluoroethylene, perfluoroethylene, polystyrene, polyvinyl chloride, and polyvinyl pyrolidone.

13. The device of claim 1, wherein the second fiber imparts additional strength.

14. The device of claim 13, wherein the second fiber imparts sufficient strength to permit the device to be freestanding devices without the assistance of a substrate.

15. The medical device of claim 1, wherein the nitric oxide predrug component is selected from the group consisting of a diazeniumdiolate, an O-alkylated diazeniumdiolate, and an O-derivatized diazeniumdiolate.

16. The medical device of claim 1, wherein the nitric oxide predrug component comprises a diazeniumdiolate.

17. The device of claim 7, wherein the activator is a proton donor.

18. The device of claim 17, wherein the activator is a buffer selected from the group consisting of phosphates, succinates, carbonates, acetates, formates, propionates, butyrates, fatty acids, and amino acids.

19. The device of claim 17, wherein the activator is water.

* * * * *